(12) United States Patent
Russo

(10) Patent No.: US 12,178,615 B2
(45) Date of Patent: Dec. 31, 2024

(54) METHODS AND APPARATUS FOR ADAPTIVE FILTERING OF SIGNALS OF CONTINUOUS ANALYTE MONITORING SYSTEMS

(71) Applicant: Ascensia Diabetes Care Holdings AG, Basel (CH)

(72) Inventor: Anthony P. Russo, New York, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 92 days.

(21) Appl. No.: 17/338,247

(22) Filed: Jun. 3, 2021

(65) Prior Publication Data

US 2021/0378599 A1 Dec. 9, 2021

Related U.S. Application Data

(60) Provisional application No. 63/112,134, filed on Nov. 10, 2020, provisional application No. 63/034,979, filed on Jun. 4, 2020.

(51) Int. Cl.
*A61B 5/00* (2006.01)
*A61B 5/145* (2006.01)
(Continued)

(52) U.S. Cl.
CPC ............ *A61B 5/725* (2013.01); *A61B 5/1451* (2013.01); *A61B 5/14532* (2013.01);
(Continued)

(58) Field of Classification Search
CPC .................. A61B 5/725; A61B 5/1451; A61B 5/14532; A61B 5/7203; A61B 5/14865;
(Continued)

(56) References Cited

U.S. PATENT DOCUMENTS

| 2010/0179409 | A1 | 7/2010 | Kamath et al. |
| 2015/0028162 | A1* | 1/2015 | Wildschek ............... G05D 1/00 244/76 C |

(Continued)

FOREIGN PATENT DOCUMENTS

| CN | 106963373 A | 7/2017 |
| CN | 110169764 A | 8/2019 |
| CN | 110584646 A | 12/2019 |

OTHER PUBLICATIONS

Chen, YangQuan, and Blas M. Vinagre. "A new IIR-type digital fractional order differentiator." Signal processing 83.11 (2003): 2359-2365. (Year: 2003).*

(Continued)

*Primary Examiner* — Jay B Shah
*Assistant Examiner* — Meghan R Kumar
(74) *Attorney, Agent, or Firm* — Erise IP, P.A.

(57) ABSTRACT

A method of filtering a signal in a continuous analyte monitoring system (CAM) includes applying adaptive filtering to the signal using an adaptive filter to generate a filtered continuous analyte monitoring signal during an analyte monitoring period, and increasing the adaptive filtering applied to the signal as a function of increasing noise on the signal. Other methods, apparatus, continuous analyte monitoring devices, and continuous glucose monitoring devices are also disclosed.

27 Claims, 10 Drawing Sheets

(51) Int. Cl.
*A61B 5/1486* (2006.01)
*G16H 10/60* (2018.01)
*G16H 40/67* (2018.01)
*G16H 50/30* (2018.01)

(52) U.S. Cl.
CPC ........ *A61B 5/14865* (2013.01); *A61B 5/7203* (2013.01); *A61B 5/7275* (2013.01); *G16H 10/60* (2018.01); *G16H 40/67* (2018.01); *G16H 50/30* (2018.01)

(58) Field of Classification Search
CPC ................ A61B 5/7275; A61B 5/6833; A61B 5/7225; A61B 5/1455; G16H 40/67; G16H 10/60; G16H 50/30
See application file for complete search history.

(56) References Cited

U.S. PATENT DOCUMENTS

| | | | |
|---|---|---|---|
| 2015/0328402 A1 | 11/2015 | Nogueira et al. | |
| 2017/0311897 A1* | 11/2017 | Faccioli | A61B 5/7203 |
| 2019/0150803 A1* | 5/2019 | Vanslyke | A61M 5/1723 |
| 2020/0138381 A1* | 5/2020 | LeBoeuf | A61B 5/02108 |
| 2020/0178865 A1* | 6/2020 | Trattler | A61B 5/14552 |
| 2021/0121073 A1* | 4/2021 | Kuenen | A61B 5/7217 |
| 2021/0267501 A1* | 9/2021 | Jachmann | A61B 5/1486 |

OTHER PUBLICATIONS

U.S. Appl. No. 17/337,133, filed Jun. 3, 2021, Russo.
International Search Report of International Application No. PCT/EP2021/064991 mailed Sep. 27, 2021.
Chen, Y.Q. et al.: "A new IIR-type digital fractional order differentiator", Signal Processing, Elsevier Science Publishers B.V. Amsterdam, NL, vol. 83, No. 11, Nov. 1, 2003 (Nov. 1, 2003), pp. 2359-2365, XP004463297, ISSN: 0165-1684, DOI: 10-1016/S0165-1684(03)00188-9, p. 2361, equation (4).
Okoniewski, P. et al.: "A concept of IIR filters with time-varying coefficients and equalised group delay response", Measurement., vol. 60, Jan. 1, 2015 (Jan. 1, 2015), pp. 13-24, XP055841596, GB; ISSN: 0263-2241, D01: 10.1016/j.measurement. 2014.09.077; the whole document.
European Patent Application 21732820.2, Communication pursuant to Rules 161(1) and 162 EPC, issued Jan. 12, 2023.
Taiwan Patent Application 110120374, First Office Action, issued Oct. 8, 2024.

* cited by examiner

METHODS AND APPARATUS FOR ADAPTIVE FILTERING OF SIGNALS OF CONTINUOUS ANALYTE MONITORING SYSTEMS

CROSS REFERENCE TO RELATED APPLICATIONS

This claims the benefit of U.S. Provisional Patent Applications Nos. 63/034,979, filed Jun. 4, 2020, and 63/112,134, filed Nov. 10, 2020, the disclosures of which are hereby incorporated by reference herein in their entireties for all purposes.

FIELD

The present disclosure relates to apparatus and methods for continuous analyte monitoring.

BACKGROUND

Continuous analyte monitoring (CAM), such as continuous glucose monitoring (CGM), has become a routine monitoring operation, particularly for individuals with diabetes. CAM can provide real-time analyte analysis (e.g., analyte concentrations) of an individual. In the case of CGM, real-time glucose concentrations of an individual can be provided. By providing real-time glucose concentrations, therapeutic and/or clinical actions may be applied in a timely fashion to the individual being monitored and a glycemic condition may be better controlled.

Improved CAM and CGM methods and apparatus are therefore desired.

SUMMARY

In some embodiments, a method of filtering a signal in a continuous analyte monitoring system is provided. The method includes applying adaptive filtering to the signal using an adaptive filter to generate a filtered continuous analyte monitoring signal during an analyte monitoring period, and increasing the adaptive filtering applied to the signal as a function of increasing noise on the signal.

In other embodiments, a method of continuous analyte monitoring (CAM) is provided. The method includes generating a CAM signal; applying adaptive filtering to the CAM signal using an adaptive filter to generate an adaptively-filtered CAM signal; and increasing attenuation of the adaptive filtering as a function of increasing noise on the CAM signal.

In other embodiments, a continuous analyte monitoring (CAM) system is provided. The system includes at least one device configured to generate a signal, and an adaptive filter configured to increase filtering of the signal as a function of increasing noise on the signal.

Other features, aspects, and advantages of embodiments in accordance with the present disclosure will become more fully apparent from the following detailed description, the claims, and the accompanying drawings by illustrating a number of example embodiments and implementations. Various embodiments in accordance with the present disclosure may also be capable of other and different applications, and its several details may be modified in various respects, all without departing from the scope of the claims and their equivalents. Accordingly, the drawings and descriptions are to be regarded as illustrative in nature, and not as restrictive.

BRIEF DESCRIPTION OF THE DRAWINGS

The drawings, described below, are for illustrative purposes only and are not necessarily drawn to scale. The drawings are not intended to limit the scope of the disclosure in any way. Like numerals are used throughout to denote the same or like elements.

DETAILED DESCRIPTION

Figure 1:
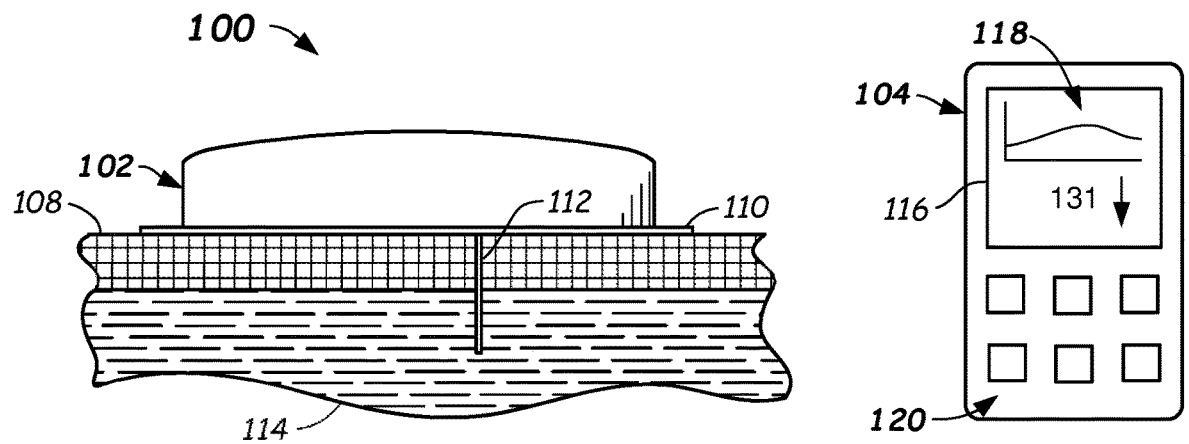
FIG. 1 illustrates a partially cross-sectioned side view and a front elevation view, respectively, of a wearable device and an external device of a continuous analyte monitoring (CAM) system according to embodiments of the disclosure.

A continuous analyte monitoring (CAM) system can measure analyte concentrations in an individual over time and report those analyte concentrations. Some CAM systems include one or more implanted biosensors that directly or indirectly sense (e.g., measure) an analyte present in a bodily fluid and generate one or more signals (e.g., sensor signals or biosensor signals) in response to the sensing. The one or more sensor signals are then processed to generate and/or calculate continuous analyte signals indicative of analyte concentrations over time. The continuous analyte signals are sometimes referred to as "CAM signals" and are reported to a user or a medical provider by way of a display, download, or other communication type.

In some embodiments, the one or more biosensors may comprise one or more probes or the like that pierce the user's skin and are located or implanted subcutaneously into interstitial fluid, for example. In other embodiments, the one or more biosensors may be optical devices that can measure subcutaneous reflectance, for example. The CAM systems may use other types of biosensors.

CAM systems that include a subcutaneous biosensor may monitor current flow between two or more electrodes on the biosensor when the biosensor is located in interstitial fluid. This current flow may be used to determine an analyte concentration (e.g., glucose concentration) in the interstitial fluid. In some embodiments, the biosensor may be contained within and inserted by a trocar (e.g., needle) configured to extend into the user's skin for subcutaneous placement of the biosensor so as to contact interstitial fluid of a user. Upon insertion, the trocar may be removed, leaving behind the implanted biosensor. The biosensor may include electrodes, such as a working electrode, a counter electrode, and/or a reference electrode, for example, that contact the user's interstitial fluid.

During continuous analyte monitoring, a voltage is applied between the electrodes, such as between the working electrode and the counter electrode, and current flow through one or more electrodes is measured. The current flow is proportional to the analyte (e.g., glucose) concentration present in the interstitial fluid. The current flow through the electrodes and the interstitial fluid may be very small, such as a few nanoamperes, which makes the CAM systems very sensitive to noise. When signals indicative of the current flow or other signals within CAM systems are subjected to noise, even a weak noise level, the resulting signal-to-noise ratio may be very low, which results in signals that are difficult to process and/or interpret. In some embodiments, the noise may cause the resulting CAM signal to be jittery, which can make the resulting CAM signal difficult to accurately interpret.

One noise source in CAM systems is caused by degradation of components within the CAM systems, such as over an analyte monitoring period. An analyte monitoring period is the time period over which a biosensor of a CAM system senses analytes. In the example of a biosensor configured to be located subcutaneously, the analyte monitoring period is the time in which the biosensor is located subcutaneously and is actively sensing. An analyte monitoring period may be 14 days or more, for example, i.e., the elapsed length of time during which the biosensor is implanted, sensing, and communicating. In one example, the biosensor properties may degrade as a function of time, which may cause signals generated by the biosensor to become increasingly noisy over the analyte monitoring period. For example, in embodiments wherein the biosensors are located in interstitial fluid, chemicals (e.g., enzymes) deposited on the biosensors that react with the interstitial fluid may degrade and/or deplete during the analyte monitoring period. In some situations, biofilms may also accumulate on the biosensors during the analyte monitoring period.

The degradation and/or depletion of the chemicals may increase or otherwise change during the analyte monitoring period, which causes the sensor signals to be increasingly noisy and/or jittery during the analyte monitoring period. In some embodiments, the sensor signals become increasingly noisy and/or jittery as the analyte monitoring period progresses. The same may occur with increasing accumulations of biofilms. The noise may be processed with the sensor signals, which yields noisy and/or jittery CAM results that are difficult to interpret or may cause a user to believe that the CAM system is not working correctly.

Other sources of noise in CAM systems include quantization noise and other noise generated during signal processing. For example, during analog-to-digital conversion, quantization noise may be generated. In some embodiments, the level of the quantization noise is dependent on the signals being converted and/or the conversion process. Thus, the quantization noise is generally not time dependent. Electrical sources may also contribute to noise within CAM systems. For example, devices used to transmit and receive signals in the CAM systems may generate extraneous noise. In other embodiments, external noise sources may increase noise on signals within CAM systems. For example, if a CAM system is operated near certain electromagnetic fields, the fields may induce noise within the CAM system. These noise levels and occurrences of the noise may be unpredictable and may cause the aforementioned issues. Other noise sources may be due to chemical reactions (e.g. oxygen deprivation).

Apparatus and methods disclosed herein reduce the effects of noise in such CAM systems by applying adaptive filtering to one or more signals in the CAM systems to generate at least one adaptively-filtered continuous analyte signal (adaptively-filtered CAM signal). The adaptive filtering is dependent on (e.g., a function of) noise on one or more signals in the CAM system. Noise reduction may be achieved, for example, by smoothing one or more signals generated in the CAM systems using adaptive filtering. The degradation of the biosensors described above and/or degradation of other components over the analyte monitoring period may vary during the monitoring period. The adaptive filtering applied to the one or more signals changes as a function of noise (e.g., signal-to-noise ratio) so as to smooth noisy signals.

Apparatus and methods disclosed herein reduce the effects of noise in CAM systems by applying adaptive filtering to one or more signals in CAM systems to generate at least one adaptively-filtered continuous analyte signal (sometime referred to herein as a "filtered signal"). Adaptive filtering and adaptive filters may measure noise levels on a signal and apply filtering as a function of the noise levels on the signal. For example, an adaptive filter or another device may measure noise levels on a signal and apply filtering or smoothing to the signal, wherein the degree of filtering or smoothing is dependent on the measured noise levels.

Various noise measurement (or estimation) techniques may be used to measure the noise on the signal. In some embodiments, point-to-point variances may be used to measure the noise on a signal. In such embodiments, a signal is measured at sample times during a time window. The time window may be immediately prior to the present time. A noise estimate may be calculated based on the standard deviation of the differences between all adjacent sample times of the signal in the time window divided by the average of the signal in the time window. The amount of adaptive filtering or smoothing may be a function of noise estimates and/or measurements. Other embodiments of noise measurements including other embodiments of point-to-point variances may be used. The adaptive filtering may include digital or analog filters. Some filtering may include exponential moving average (EMA) filtering, including double EMA and triple EMA filtering.

The adaptive filtering described herein may be applied to different signals within the CAM system including, e.g., working electrode current signals, background current signals, CAM signals, estimated device sensitivity signals, and estimated analyte (e.g., glucose) concentration signals. The adaptive filtering smooths the signals and/or reduces the effects of noise and/or algorithm artifacts, which improves a user's ability to interpret the analyte concentrations. In some embodiments, the filtering is changed by adjusting smoothing parameters of an adaptive filter as a function of noise.

These and other apparatus and methods are described in detail with reference to FIGS. 1-9. Embodiments of adaptive filtering apparatus and methods are described herein with reference to continuous glucose monitoring (CGM) systems. However, the adaptive filtering apparatus and methods described herein may be applied to other continuous analyte monitoring (CAM) systems that measure analytes, such as cholesterol, lactate, uric acid, and alcohol, for example.

Reference is now made to FIG. 1, which illustrates an example of a continuous glucose monitoring (CGM) system 100 including a wearable device 102 and an external device 104. As described herein, the wearable device 102 measures glucose concentrations and the external device 104 displays the glucose concentrations. In some embodiments, the wearable device 102 may also display glucose concentrations. The wearable device 102 may be attached (e.g., adhered) to the skin 108 of a user such as by an adhesive-backed layer 110, for example.

The wearable device 102 may include a biosensor 112 that may be located subcutaneously in interstitial fluid 114 of a user and may directly or indirectly measure glucose concentrations. The wearable device 102 may transmit the glucose concentrations to the external device 104, where the glucose concentrations may be displayed on an external display 116. The external display 116 may display different formats of glucose concentrations, such as individual numbers, graphs, and/or tables. In the example embodiment of FIG. 1, the external display 116 is displaying a graph 118 showing past and present glucose concentrations and a number indicating a glucose concentration from a most recent glucose calculation. The external display 116 may also display glucose trends as noted by the downward arrow 131 shown on the external display 116, indicating that the user's blood glucose level is currently falling. The external display 116 may display different or additional data in other formats. In some embodiments, the external device 104 may include a plurality of buttons 120 or other input devices that enable users to select data and/or data formats displayed on the external display 116.

Figure 2A:
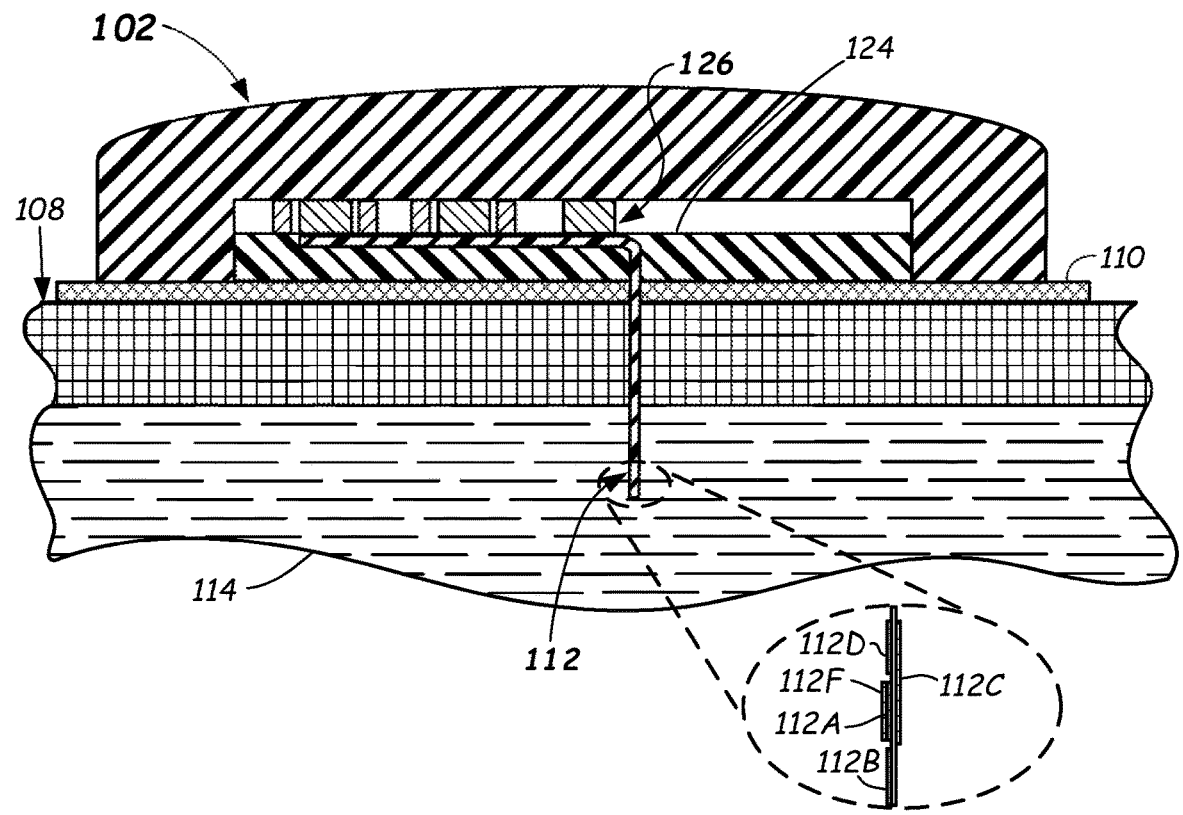
FIG. 2A illustrates a cross-sectioned side view of a wearable device of a CAM system attached to a skin surface according to embodiments of the disclosure.

Reference is now made to FIG. 2A, which illustrates a partial, cross-sectioned side view of the wearable device 102 attached to the skin 108 of a user. The biosensor 112 may be located in interstitial fluid 114 beneath the skin 108 of a user.

In the embodiment of FIG. 2A, the biosensor 112 may include a working electrode 112A, a reference electrode 112B, and a counter electrode 112C that may each contact the interstitial fluid 114 as described further below. In some embodiments, the biosensor 112 may include fewer or more electrodes and other electrode configurations. For example, in some embodiments, a second working electrode (e.g., a background electrode) may be employed. The electrodes 112A, 112B, and 112C may be made with and/or coated with one or more chemicals, such as one or more enzymes that react with specific chemical analytes within the interstitial fluid 114. The reactions may change current flow through one or more of the electrodes 112A, 112B, and 112C, which is detected by the wearable device 102 and is used to calculate glucose concentrations as described herein.

Figure 2B:
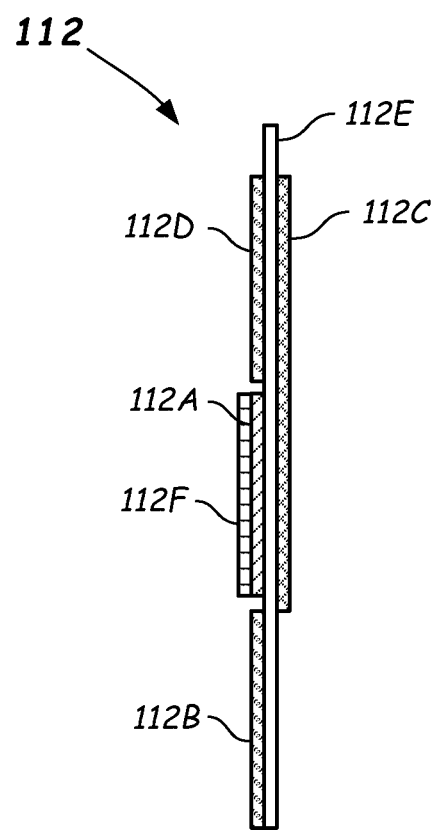
FIG. 2B illustrates a partially cross-sectioned side elevation view of a portion of a biosensor of a CAM system according to embodiments of the disclosure.

FIG. 2B illustrates a cross-sectioned side schematic enlarged partial view of an embodiment of the biosensor 112 in accordance with embodiments provided herein. In some embodiments, the biosensor 112 may include a working electrode 112A, a counter electrode 112C, and a background electrode 112D. The working electrode 112A may include a conductive layer coated with a chemical 112F, which reacts with a glucose-containing solution in a reduction-oxidation reaction, which affects the concentration of charge carriers and time-dependent impedance of the biosensor 112. In some embodiments, the working electrode 112A may be formed from platinum or surface roughened platinum. Other working electrode materials may be used. Example chemical catalysts (e.g., enzymes) for the working electrode 112A include glucose oxidase, glucose dehydrogenase, or the like. The enzyme component may be immobilized onto the electrode surface by a cross-linking agent such as glutaraldehyde, for example. An outer membrane layer (not shown) may be applied onto the enzyme layer to protect the overall inner components including the electrode and the enzyme layer. In some embodiments, a mediator such as ferricyanide or ferrocene may be employed. Other chemical catalysts and/or mediators may be employed.

In some embodiments, the reference electrode 112B may be formed from Ag/AgCl. The counter electrode 112C and/or the background electrode 112D may be formed from a suitable conductor such as platinum, gold, palladium, or the like. Other suitably conductive materials may be used for the reference electrode 112B, the counter electrode 112C, and/or the background electrode 112D. In some embodiments, the background electrode 112D may be identical to the working electrode 112A, but without the chemical catalyst and mediator. The counter electrode 112C may be isolated from the other electrodes by an isolation layer 112E (e.g., polyimide or another suitable material).

The biosensor 112 may include other items and materials that are not shown. For example, the biosensor 112 may include other insulators and the like that electrically insulate the electrodes from one another. The biosensor 112 may also include conductors and the like that electrically couple the electrodes to components in the wearable device 102.

The above-described chemicals on or in the working electrode 112A, the reference electrode 112B, the counter electrode 112C, and the background electrode 112D may become depleted and/or contaminated during an analyte (e.g., glucose) monitoring period. The depletion and/or contamination may cause signals generated by or in conjunction with the biosensor 112 to be noisy and/or jittery as a function of time as described herein. In addition, biofilms may accumulate on the electrodes 112A, 112B, 112C, and/or 112D, which may cause signals generated by the biosensor 112 to become noisier. The adaptive filtering described herein filters or smooths one or more signals within the CGM system 100 to counter effects of the noisy and/or jittery signals.

Returning to FIG. 2A, the wearable device 102 may include a substrate 124 (e.g., a circuit board) on which components 126 of the wearable device 102 may be located. Portions of the substrate 124 may be made of non-conductive materials such as plastic or ceramic. In some embodiments, the substrate 124 may include a laminated material. The substrate 124 may include electrical traces (not shown) that conduct current to components within or attached to the substrate 124, such as the biosensor 112. For example, conductors (not shown) may electrically couple the electrodes 112A, 112B, and 112C to the components 126.

The components 126 may apply a bias voltage across two or more of the electrodes 112A, 112B, 112C, 112D located in the interstitial fluid 114, which results in a bias sensor current flowing through the biosensor 112. Some of the components 126 may be part of circuitry that may measure the sensor current and generate a measured current signal $I_{MEAS}$. In some embodiments, chemicals (enzymes, etc.) on or within the electrodes 112A, 112B, and 112C change impedance in response to contact with glucose or other chemicals or analytes present in the interstitial fluid 114. Thus, the resulting measured current signal $I_{MEAS}$ may be proportional to one or more analytes (e.g., glucose) present in the interstitial fluid 114. During the glucose monitoring period, the chemicals on the electrodes 112A, 112B, and 112C may deteriorate and/or deplete, which may cause the sensor current and the measured current signal $I_{MEAS}$ to become noisy (e.g., jittery) as described above.

As described herein, adaptive filtering may be applied to the measured current signal $I_{MEAS}$ and/or other signals in the wearable device 102 and/or the external device 104 to reduce the effects of changes in noise in the signals. In some embodiments, adaptive filtering may be applied to the resulting CGM signal to reduce noise (e.g., jitter) on the CGM signal. As described herein, the adaptive filtering may change (e.g., increase) attenuation in stop-bands and/or change (e.g., increase) the order of adaptive filter(s) as a function of noise.

Figure 3A:
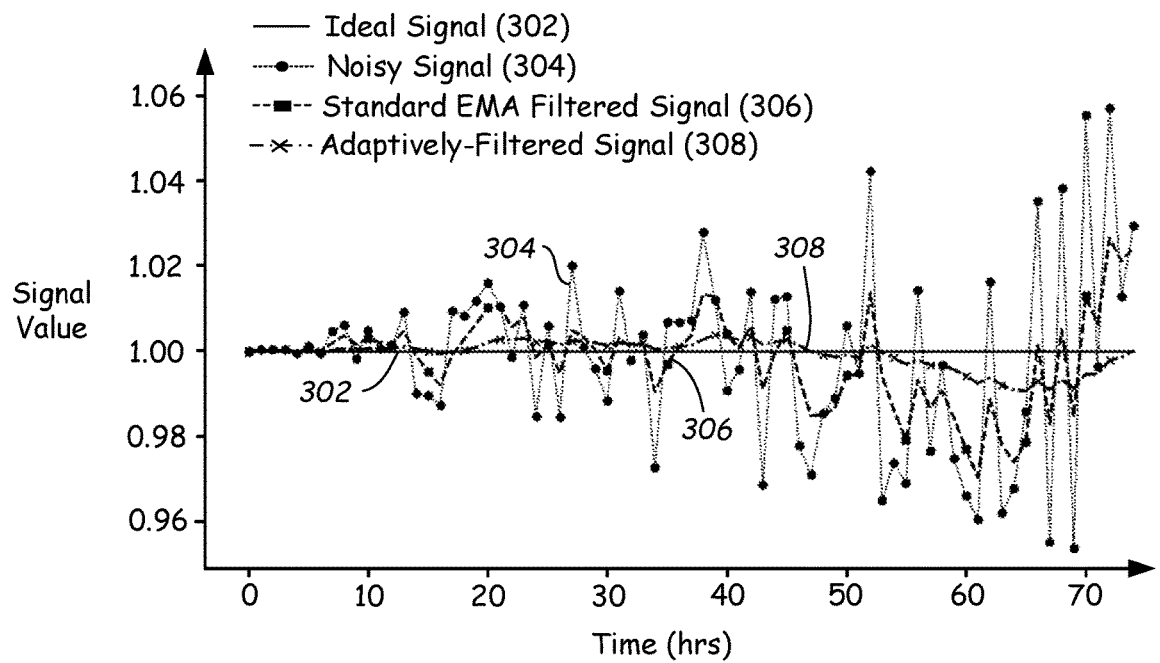
FIG. 3A is a graph illustrating a signal within a CAM system, the signal with noise (noisy signal), the noisy signal with standard filtering applied, and the noisy signal with adaptive filtering applied according to embodiments of the disclosure.

Reference is now made to FIG. 3A, which is a graph illustrating examples of different filtering effects, including adaptive filtering, on a noisy signal. In the example of FIG. 3A, an ideal signal 302 (solid line) is normalized to a signal value of 1.00. A noisy signal 304, which is the ideal signal 302 with noise added, is shown as a fine-dotted line with dots representing data points thereon. In the example of FIG. 3A, the magnitude of the noisy signal 304 increases as a function of time, but the magnitude of the noisy signal may be random in some embodiments.

A standard exponential moving average (EMA) filtered signal 306, which is the noisy signal 304 after being subjected to standard (EMA) filtering, is shown as a dashed line with squares located therein. The standard EMA filtering is not time or noise dependent and, thus, the filtering applied by the standard EMA filtering does not vary as a function of noise. As shown in FIG. 3A, noise on the standard EMA filtered signal 306 continues to increase randomly and/or over time. In other examples, random noise levels may appear at random times on the noisy signal 304. When conventional filtering is applied to signals in a CGM system, the signal-to-noise ratio of these signals decreases as a function of noise, which may render data provided by the CGM system 100 (FIG. 1) inaccurate or difficult to interpret.

An adaptively-filtered signal 308 (sometimes referred to as the "filtered signal 308") is the result of the noisy signal 304 after being subjected to adaptive filtering (e.g., adaptive EMA filtering) and is shown in FIG. 3A as a dashed line with x's located thereon. The adaptive filtering that produced the filtered signal 308 shown in FIG. 3A increases as a function of increasing noise. For example, smoothing of the noisy signal 304 may increase as a function of noise. Thus, as the amplitude of noise on the ideal signal 302 increases as shown by the noisy signal 304, the resulting filtered signal 308 is more heavily smoothed or filtered. In some embodiments, attenuation of the adaptive filter may increase as a function of noise and/or time. In some embodiments, the adaptive filter may include one or more low-pass filters wherein attenuation in the stop band may increase as a function of noise. When applied to a CGM system, the adaptive filtering reduces noise that increases during a glucose monitoring period and other noise, such as random noise. Accordingly, the resulting filtered signal 308 that has adaptive filtering applied thereto more closely follows the ideal signal 302. When applied to a CGM system, the adaptive filtering reduces noise that increases and/or changes during an analyte (e.g., glucose) monitoring period, which enables the user of a CGM system to receive more accurate information regarding analyte (e.g., glucose) concentrations.

Figure 3B:
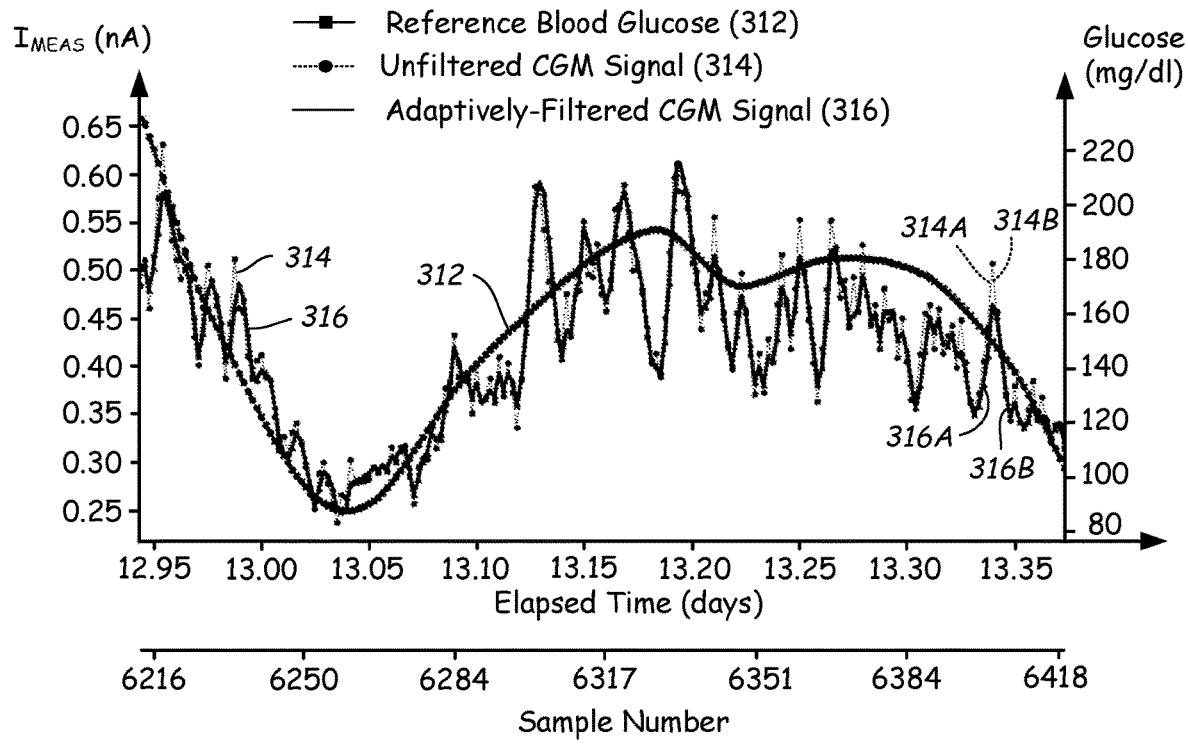
FIG. 3B is a graph illustrating an example of blood glucose concentrations of an individual, an unfiltered CGM signal, and an adaptively-filtered CGM signal according to embodiments of the disclosure.

Additional reference is made to FIG. 3B, which is a graph showing an example of reference blood glucose concentrations 312, an unfiltered CGM signal 314, and an adaptively-filtered CGM signal 316 (sometimes referred to as the "filtered CGM signal 316"). The horizontal axis of the graph of FIG. 3B references elapsed time in days and by sample number. Note that the examples shown in the graph of FIG. 3B are recorded during a portion of the analyte (e.g., glucose) monitoring period from the end of the twelfth day to about eight hours into the thirteenth day. The unfiltered CGM signal 314 may be an unfiltered CGM signal generated by the wearable device 102 (FIG. 1) and/or the external device 104 that measures and/or calculates analyte (e.g., glucose) concentrations of a user. The filtered CGM signal 316 may be generated by applying adaptive filtering to the unfiltered CGM signal 314 and/or one or more other signals used to generate the unfiltered CGM signal 314.

In some embodiments, one or more signals generated by biosensor(s) within the wearable device 102 may have the adaptive filtering applied thereto, which may yield the adaptive-filtered CGM signal 316 (sometimes referred to as the filtered CGM signal 316). For example, the noisy signal 304 (FIG. 3A) may be a signal generated by a biosensor within the wearable device 102. The filtered CGM signal 316 may be the result of applying adaptive filtering to the noisy signal 304. As shown in FIG. 3B, the resulting filtered CGM signal 316 generally follows the reference blood glucose concentrations 312 and is much smoother than the unfiltered CGM signal 314.

Figure 4A:
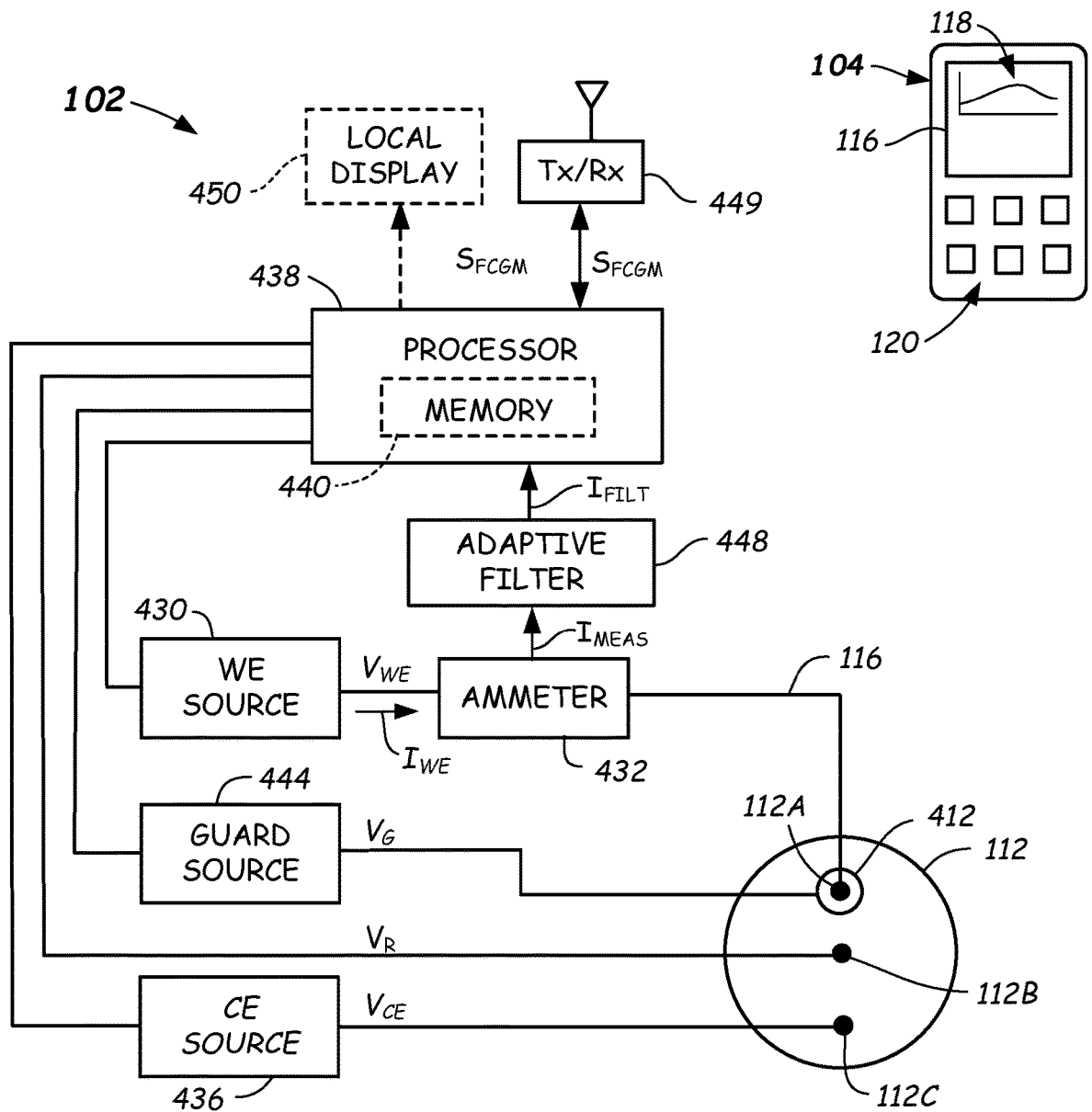
FIG. 4A is a schematic diagram showing an example of circuitry components within a wearable device of a CGM system according to embodiments of the disclosure.

Additional reference is now made to FIG. 4A, which illustrates a schematic diagram of an embodiment of example circuitry of the wearable device 102 (FIG. 2A). In the embodiment shown in FIG. 4A, the biosensor 112 does not include the background electrode 112D (FIG. 2B). As shown in FIG. 4A, the working electrode 112A may be surrounded by a guard ring 412 that reduces stray current from interfering with the working electrode 112A. In some embodiments, the guard ring 412 may operate at the same potential as the working electrode 112A. The working electrode 112A may be coupled to a working electrode source 430 by way of a current measuring device, such as an ammeter 432. The ammeter 432 measures a working electrode current $I_{WE}$ generated by the working electrode source 430 and generates the measured current signal $I_{MEAS}$, which is indicative of the working electrode current $I_{WE}$. During operation of the wearable device 102, the working electrode source 430 may generate a voltage $V_{WE}$ that is applied to the working electrode 112A resulting in the working electrode current $I_{WE}$ passing through the working electrode 112A. The ammeter 432 measures the working electrode current $I_{WE}$ and generates the measured current signal $I_{MEAS}$.

In the embodiment of FIG. 4A, the wearable device 102 may include a counter electrode source 436 electrically coupled to the counter electrode 112C that generates a counter electrode voltage $V_{CE}$. The working electrode current $I_{WE}$ is therefore proportional to the difference between the working electrode voltage $V_{WE}$ and the counter electrode voltage $V_{CE}$, divided by the impedances of the interstitial fluid 114 (FIG. 2) and the impedances of the electrodes in the biosensor 112. In some embodiments, a current sunk by the counter electrode source 436 is equal to the working electrode current $I_{WE}$.

Both the working electrode source 430 and the counter electrode source 436 may be coupled to and controlled by a processor 438. The processor 438 may include memory 440 having computer-readable instructions stored therein that cause the processor 438 to send instructions to the working electrode source 430 and the counter electrode source 436. The instructions may cause the working electrode source 430 and the counter electrode source 436 to output predetermined voltages (e.g., $V_{WE}$ and $V_{CE}$). The memory 440 may also include instructions that cause the processor to perform other functions as described herein, such as applying adaptive filtering.

The circuitry of the embodiment of the wearable device 102 shown in FIG. 4A may include a guard source 444 that is coupled to the guard ring 412 and supplies a guard voltage $V_G$ to the guard ring 412. The guard source 444 may also be coupled to the processor 438 and may receive instructions from the processor 438 to set a specific guard voltage $V_G$. The reference electrode 112B may be coupled to the processor 438 and may supply a reference voltage $V_R$ to the processor 438. The processor 438 may use the reference voltage $V_R$ to set values of the working voltage $V_{WE}$ and the counter voltage $V_{CE}$.

As described above, the ammeter 432 may generate the measured current signal $I_{MEAS}$, which is a measure of the working electrode current $I_{WE}$. In conventional CGM systems, if noise is present on the working electrode current $I_{WE}$, the measured current signal $I_{MEAS}$ and the resulting CGM signal may be noisy. For example, the resulting CGM signal may be similar to the unfiltered CGM signal 314 of FIG. 3B. In the embodiment of FIG. 4A, an adaptive filter 448 applies adaptive filtering to the measured current signal $I_{MEAS}$ prior to the measured current signal $I_{MEAS}$ being processed and/or received by the processor 438. The adaptive filter 448 outputs a filtered measured current signal $I_{FILT}$, which may be processed by the processor 438 to render the adaptively-filtered CGM signal 316.

Figure 5A:
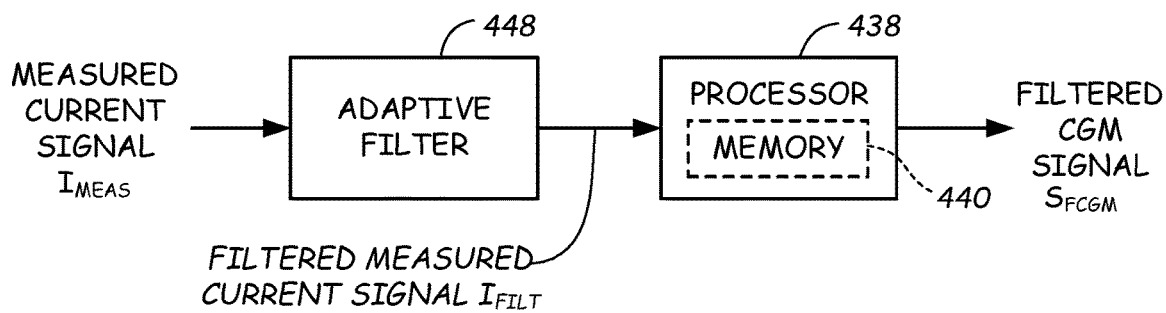
FIG. 5A is a block diagram showing an example of adaptive filtering in an embodiment of a wearable device of a CGM system according to embodiments of the disclosure.

Additional reference is made to FIG. 5A, which is a block diagram showing functions of a portion of the circuitry of FIG. 4A. As shown in the example of FIG. 5A, the adaptive filtering is applied by the adaptive filter 448 to the measured current signal $I_{MEAS}$ prior to the processor 438 processing the measured current signal $I_{MEAS}$. In other embodiments described herein, the adaptive filtering may be performed and/or applied by the processor 438 and/or to other signals within the external device 104 (FIG. 1). The adaptive filtering or other components or processes may include components or methods that measure noise, such as signal-to-noise ratios, as described above.

The measured current signal $I_{MEAS}$ may be similar to the noisy signal 304 shown in FIG. 3A. As described herein, the biosensor 112 may degrade over time, which may be one cause of the noise on the measured current signal $I_{MEAS}$. As described above, external noise sources and noise incurred during signal processing may also cause noise on the measured current signal $I_{MEAS}$. If the processor 438 processes the noisy measured current signal $I_{MEAS}$, the resulting CGM signal may be noisy like the unfiltered CGM signal 314 shown in FIG. 3B. The filtered measured current signal $I_{FILT}$ output by the adaptive filter 448 is smoother (e.g., less noisy and/or jittery) than the measured current signal $I_{MEAS}$, so the resulting CGM signal is smoother. For example, the filtered measured current signal $I_{FILT}$ may be similar to the filtered signal 308 of FIG. 3A, which more closely follows an ideal measured current signal (e.g., without noise), such as the ideal signal 302 in FIG. 3A. The resulting CGM signal ($S_{FCGM}$) is similar to the filtered CGM signal 316 of FIG. 3B, which generally follows the reference blood glucose concentrations 312 and is much smoother than the unfiltered CGM signal 314. Thus, the adaptive filtering applied to the measured current signal $I_{MEAS}$ provides a CGM signal $S_{FCGM}$ that more closely follows the blood glucose levels of the user and may be easier for the user of the wearable device 102 (FIG. 1) to interpret.

Embodiments of the adaptive filter 448 include analog and digital filters. In some embodiment, the adaptive filter 448 may be an analog or digital low-pass filter, wherein the pass band includes frequencies of natural fluctuations in analyte (e.g., glucose) concentrations. In some embodiments, the adaptive filter 448 may be an infinite impulse response (IIR) filter or a finite impulse response filter (FIR). In some embodiments, the adaptive filter 448 may apply an exponential moving average (EMA) to the measured current signal $I_{MEAS}$ or other signals. The attenuation of the low-pass filter may increase as a function of increasing noise such that greater attenuation is applied during periods when higher noise levels are present on the measured current signal $I_{MEAS}$ or other signals. In some embodiments, the adaptive filter 448 may be an analog low-pass filter, wherein the order of the low-pass filtering may increase as a function of noise. In some embodiments, the cut-off frequencies of the filters may change as a function of noise and/or the frequency components of the noise.

Figure 5B:
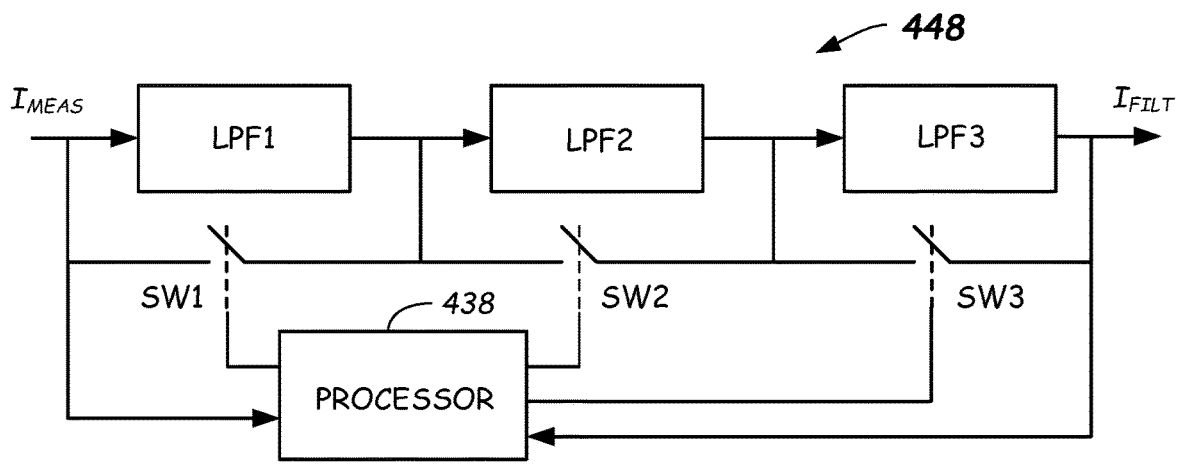
FIG. 5B is a schematic diagram of an adaptive filter implemented as a plurality of low-pass filters coupled in series according to embodiments of the disclosure.

Additional reference is made to FIG. 5B, which illustrates an example of the adaptive filter 448 implemented as a plurality of low-pass filters, such as in a filter bank, which are referenced individually as a first low-pass filter LPF1, a second low-pass filter LPF2, and a third low-pass filter LPF3, coupled in series. The adaptive filter 448 may include fewer or more low-pass filters. The adaptive filter 448 may also include a switch coupled in parallel with each of the low-pass filters LPF1, LPF2, LPF3. In the embodiment of FIG. 5B, the switches are referred to individually as a first switch SW1, a second switch SW2, and a third switch SW3. The states of the switches SW1, SW2, SW3 may be controlled by the processor 438. The amount of adaptive filtering applied by the adaptive filter 448 may be adjusted by opening or closing the switches SW1, SW2, SW3. For example, when little or no noise is present, all the switches SW1, SW2, SW3 may be closed so no filtering is applied. During time periods when higher noise levels are present, all or some of the switches SW1, SW2, SW3 may be opened to apply more filtering as a function of noise.

In some embodiments, the processor 438 may monitor the measured current signal $I_{MEAS}$ input into the adaptive filter 448 and the filtered measured current signal $I_{FILT}$ output by the adaptive filter 448. The processor 438 may measure noise on the measured current signal $I_{MEAS}$ and apply adaptive filtering via the adaptive filter 448 as a function of the noise. The processor 438 may also monitor the filtered measured current signal $I_{FILT}$ to determine if more or less adaptive filtering is warranted. In some embodiments, the processor 438 may only monitor either the measured current signal $I_{MEAS}$ or the filtered measured current signal $I_{FILT}$ and adjust the adaptive filtering accordingly.

Figure 6:
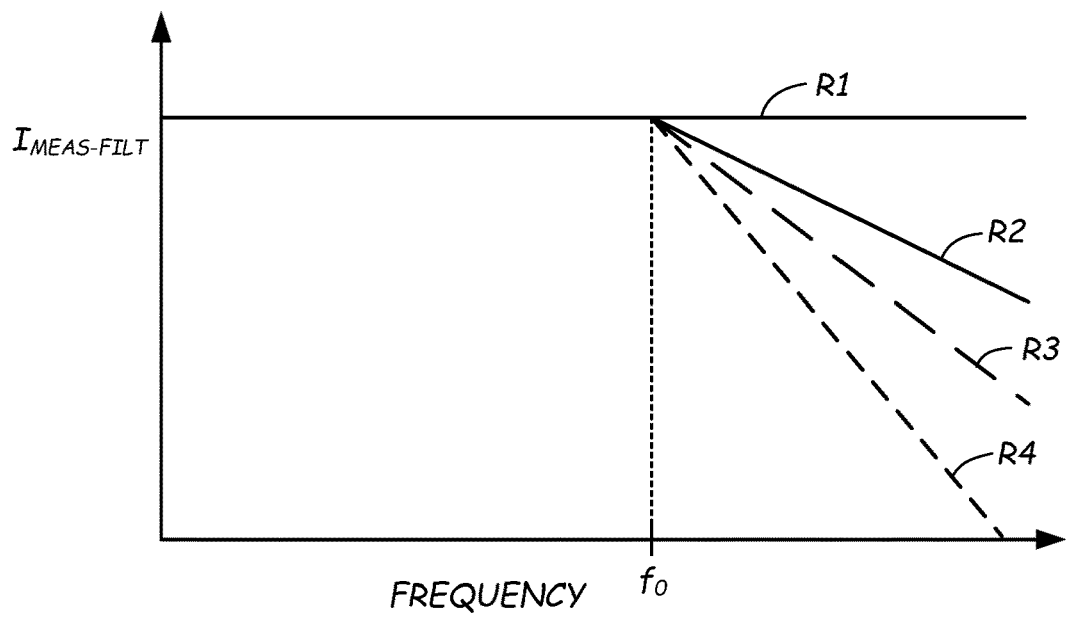
FIG. 6 is a graph showing example adaptive filter responses versus frequency over different signal-to-noise ratios (SNR1 through SNR4) according to embodiments described herein.
Figure 7:
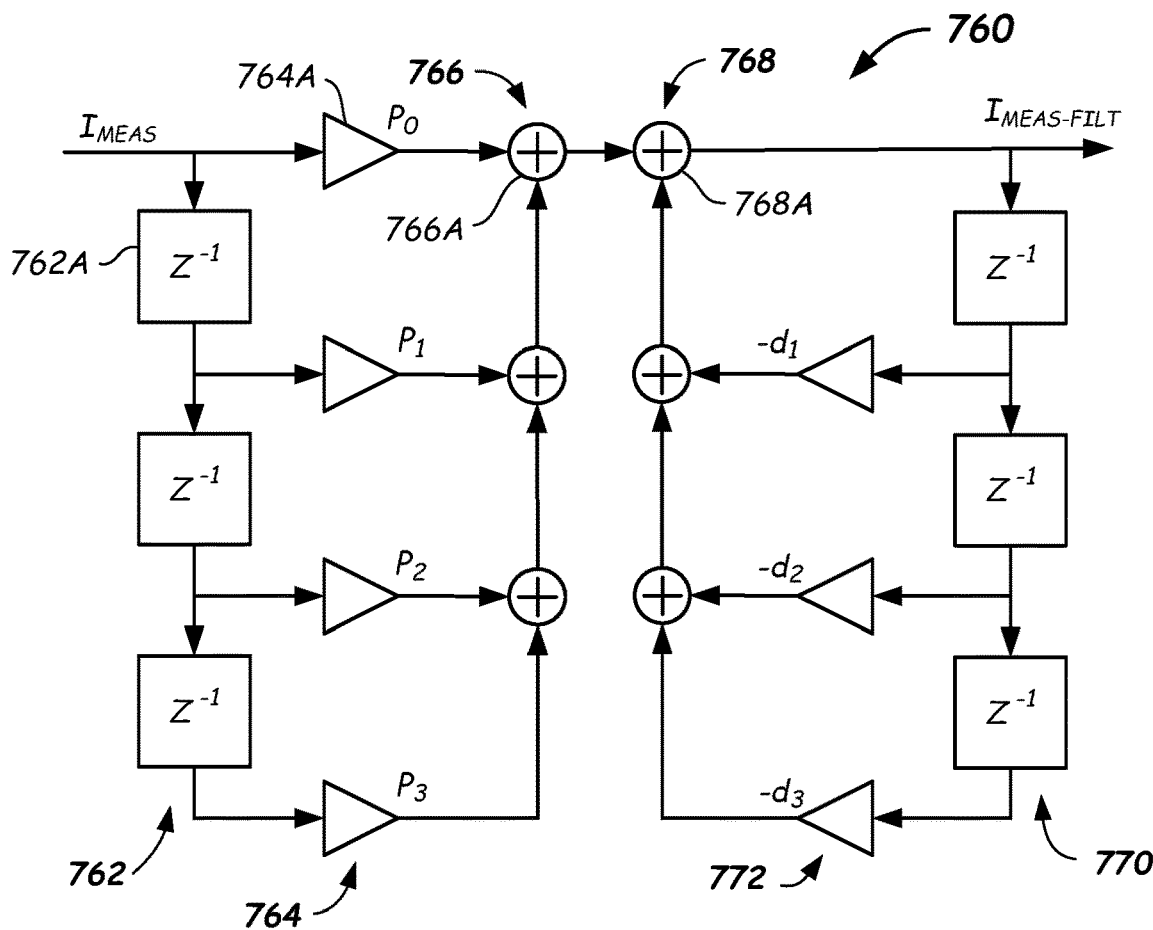
FIG. 7 illustrates a block diagram of an example of an infinite impulse response filter according to embodiments of the disclosure.

Additional reference is made to FIG. 6, which is a graph showing example filter responses as a function of noise for the adaptive filter 448, wherein the adaptive filter 448 is a low-pass filter having a cutoff frequency $f_0$. The graph of FIG. 6 is described below with reference to the adaptive filter 448 of FIG. 5B. However, other adaptive filters, such as adaptive IIR filters may produce identical or similar results. When a first noise level R1 is present on a signal, no filtering may be applied by the adaptive filter 448. The first noise level R1 is the least noise level on the signal. For example, early during a glucose monitoring period or when the wearable device 102 (FIG. 1) is not operated in a noisy environment, no filtering may be required. When a second noise level R2 is present on the signal, the adaptive filter 448 may function as a first order low-pass filter. The second noise level R2 may be greater than the first noise level R1. In some embodiments, the second noise level R2 may be prominent during a second time period as the biosensor 112 deteriorates. As shown in FIG. 6, the attenuation in the stop band is minimal when the second noise level R2 is present. The filtering applied when the second noise level R2 is present may be achieved by opening one of the switches, such as SW1.

When a third noise level R3 is present on the signal, the low-pass filter may be a higher order filter than when the second noise level R2 is present on the signal. The third noise level R3 is greater than the second noise level R2. With regard to the adaptive filter 448 of FIG. 5B, two switches, such as switches SW1 and SW2 may be opened by the processor 438. When a fourth noise level R4 is present on the signal, the low-pass filter may be a higher order filter than when the third noise level R3 is present on the signal. The fourth noise level R4 is greater than the third noise level R3. With regard to the adaptive filter 448 of FIG. 5B, all three switches SW1, SW2, and SW3 may be opened by the processor 438.

In some embodiments, the adaptive filter 448 may change the cutoff frequency $f_0$ as different noise levels are present on the signal. For example, higher noise levels on the signals may cause the adaptive filter 448 to filter higher or lower frequency components. For example, the cutoff frequency $f_0$ may change as the frequency components of the noise change. In some embodiments, the cutoff frequency $f_0$ may be higher than natural or expected fluctuations of signals in the CGM system 100.

In some embodiments, the adaptive filter 448 may be a digital filter, such as a FIR (finite impulse response) filter or an IIR (infinite impulse response) filter, for example. Other types of digital filters may be used. Additional reference is made to FIG. 7, which is a block diagram of an example embodiment of an IIR filter 760 that may be used in the adaptive filter 448. Other configurations of digital filters and IIR filters may be used. The IIR filter 760 receives the measured current signal $I_{MEAS}$ (or another signal), which is a digital signal. In some embodiments, the ammeter 432 (FIG. 4A) generates the digital signal and in other embodiments, the circuitry of FIG. 4A includes an analog-to-digital converter (not shown) that can digitize the measured current signal $I_{MEAS}$. In other embodiments, the IIR filter 760 may be used to filter other signals, such as an unfiltered CGM signal, in the CGM system 100 (FIG. 1).

The measured current signal $I_{MEAS}$ is received into a feedforward side of the IIR filter 760 at a first unit delay 762A of a series of unit delays 762 and a first multiplier 764A of a series of multipliers 764. The outputs of the multipliers 764 are output to a plurality of adders 766, including a first adder 766A. The output of the first adder 766A is input to a first adder 768A of a series of adders 768 on the feedback side of the IIR filter 760. The output of the first adder 768A is the output of the IIR filter 760. The output is fed to a series of unit delays 770, which output to a series of multipliers 772. The outputs of the multipliers 772 are input to the adders 768. The filtering of the IIR filter 760 is established by the coefficients $P_0$-$P_3$ of the multipliers 764 and coefficients $-d_1$ to $-d_3$ of the multipliers 772, which may provide the adaptive filtering described herein.

Other embodiments of adaptive filtering are described below with respect to a generic signal S(t) in the CGM system 100. In these embodiments, a filter F is applied to a signal S(t) to obtain a smoother output S'(t) as follows:

$$S'(t)=F(S(t)) \qquad \text{Equation (1)}$$

When applied to the embodiment of FIG. 4A, the filter F may be the adaptive filter 448 and the signal S(t) may be the measured current signal $I_{MEAS}$, an unfiltered CGM signal, or another signal, for example. In adaptive filtering, the filter F may be dependent on noise, so that Equation (1) yields Equation (2) as follows:

$$S'(t)=F(R(t),S(t)) \qquad \text{Equation (2)}$$

wherein R(t) is a calculated or measured noise level at any given time.

The adaptive (e.g., noise dependent) filtering of Equation (2) may yield Equation (3) as follows:

$$S'(t)=\text{alpha}*S(t)+(1-\text{alpha})*S'(t-1) \qquad \text{Equation (3)}$$

wherein alpha is a value less than or equal to 1.0. When alpha equals 1.0, there is no smoothing (e.g., filtering) of the signal S(t). As alpha is reduced, the smoothing of the signal S(t) increases. In embodiments where the adaptive filter 448 is a digital filter, such as an IIR filter, and the signal S is a digital signal S(n), Equation (3) may be written in the discrete domain as F(n, S(n)) as shown in Equation (4) as follows:

$$S'(n)=\text{alpha}*S(n)+(1-\text{alpha})*S'(n-1) \qquad \text{Equation (4)}$$

The smoothing may be applied by way of an exponential moving average (EMA). There are variations of the filtering/smoothing method. Two variations are referred to as DEMA and TEMA (double and triple EMA, respectively) that may be used in the adaptive filter 448. To make the filtering change as a function of noise on the signal, alpha may be made to change as a function of noise. For example, alpha is made to decrease as a function of increasing noise per Equation (5) as follows:

$$\text{alpha}(R)=\text{baseAlpha}-\text{noiseEstimate}*K \qquad \text{Equation (5)}$$

wherein R is a noise level and baseAlpha may be a predetermined value and may be a nominal (e.g., maximum) value of alpha that may be determined during design of the wearable device 102 (FIG. 1) and which, in some embodiments, may never change. K is a constant used to control the rate of change or responsiveness of alpha(R). The term noiseEstimate is a measured, calculated, or estimated noise on the signal and may be the value R. In some embodiments, baseAlpha may range from about 0.3 to about 0.5 and K is chosen so that alpha(R) is less than or equal to baseAlpha/2 when noiseEstimate is at its maximum value or maximum allowed value.

In some embodiments, alpha(R) may be greater than a minimum value to prevent too much smoothing. In other embodiments, alpha(R) may vary in a non-linear way as a function of noise. In some embodiments, the filtering may be restricted to certain time periods, etc. In some examples, the smoothing or filtering may commence at a time after the glucose monitoring period starts. In some embodiments, the smoothing or filtering may commence at least twenty-four hours after the start of the glucose monitoring period. In some embodiments, the filtering may be applied to any or all of the following: working electrode current $I_{WE}$, current through the reference electrode, the CGM signal, the measured current signal $I_{MEAS}$, and/or the like, for example.

Referring again to the circuitry of FIG. 4A, the processor 438 may receive the filtered measured current signal $I_{FILT}$ and calculate the CGM signal based at least in part on the filtered measured current signal $I_{FILT}$. For example, instructions (e.g., programs) stored in the memory 440 may cause the processor 438 to process the filtered measured current signal $I_{FILT}$ to calculate or estimate the glucose concentration in the interstitial fluid 114 (FIG. 2) and generate the filtered CGM signal $S_{FCGM}$. The filtered CGM signal $S_{FCGM}$ may reflect other analytes and may be referred to as an adaptively-filtered CAM signal. Because the filtered measured current signal $I_{FILT}$ is smoothened, the resulting filtered CGM signal $S_{FCGM}$ will also be smoothened relative to a CGM signal calculated using an unfiltered current measurement signal such as the measured current signal $I_{MEAS}$. In some embodiments, the adaptive filter 448 may filter the measured current signal $I_{MEAS}$ and another adaptive filter implemented in the processor 438 may further filter or smooth the CGM signal to produce the filtered CGM signal $S_{FCGM}$.

The filtered CGM signal $S_{FCGM}$ may be output by the processor 438 to a transmitter/receiver 449. The transmitter/receiver 449 may transmit the filtered CGM signal $S_{FCGM}$ to an external device, such as the external device 104 for processing and/or display on the external display 116. In some embodiments, the processor 438 may transmit the filtered CGM signal $S_{FCGM}$ to an optional local display 450 located on the wearable device 102 wherein the filtered CGM signal $S_{FCGM}$ and/or other information can be displayed.

Figure 4B:
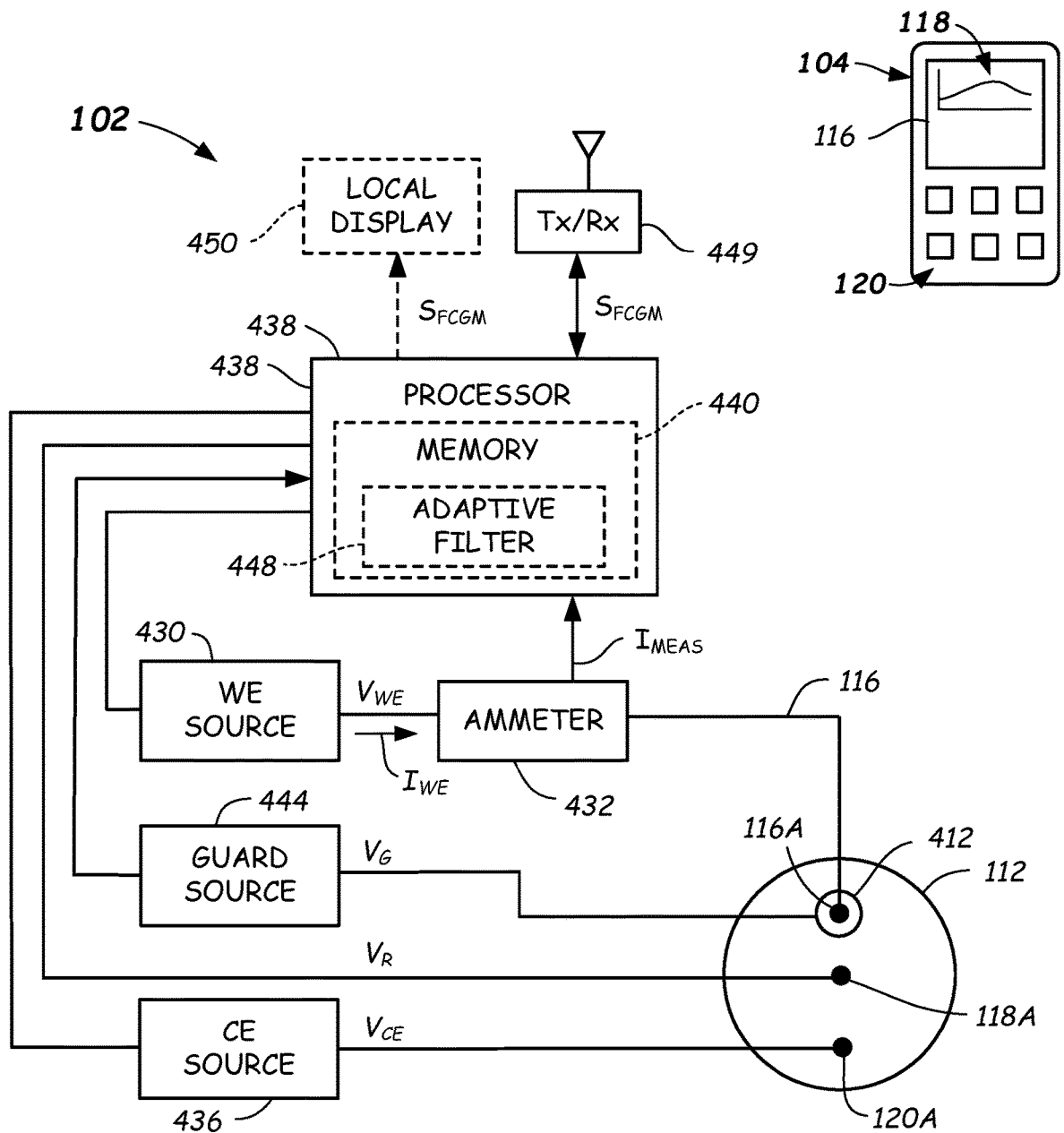
FIG. 4B is a schematic diagram showing an example of circuitry components within a wearable device that can communicate with an external device of a CGM system according to embodiments of the disclosure.
Figure 5C:
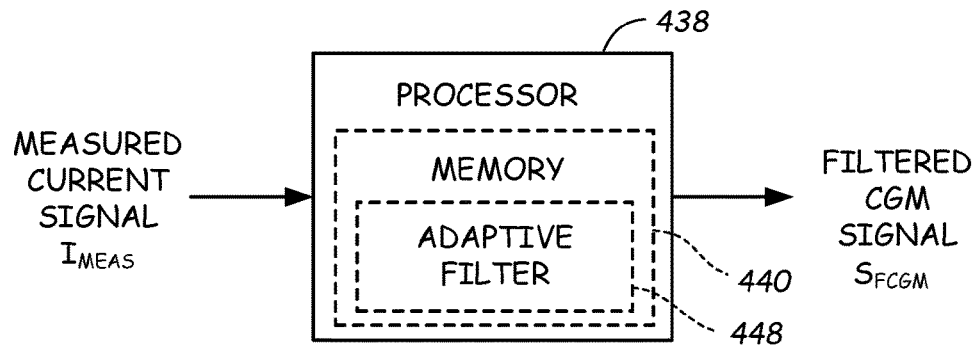
FIG. 5C is a block diagram showing an example of signal processing including adaptive filtering in an embodiment of a wearable device of a CGM system according to embodiments of the disclosure.

Reference is now made to FIG. 4B, which illustrates another embodiment of circuitry that may be configured in the wearable device 102 (FIG. 1). In the embodiment of FIG. 4B, the adaptive filter 448 is implemented in the processor 438. For example, the adaptive filter 448 may be a digital filter wherein instructions for adaptive filtering are stored in the memory 440 and executed by the processor 438. The processor 438 may apply the adaptive filtering or smoothing described in Equation (4) to the measured current signal $I_{MEAS}$, the unfiltered CGM signal, or another signal. The filtered CGM signal $S_{FCGM}$ may be output to the transmitter/receiver 449 to be transmitted to an external device, such as the external device 104. The filtered CGM signal $S_{FCGM}$ may also be transmitted to the optional local display 450 for display as described above. A block diagram of the adaptive filtering of the embodiment of FIG. 4B is shown in FIG. 5C. As shown in FIG. 5C, the measured current signal $I_{MEAS}$ is received and processed by the processor 438, which outputs the filtered CGM signal $S_{FCGM}$.

The adaptive filter 448 may be implemented in the processor 438 as described above. Accordingly, the adaptive filter 448 may apply a smoothing function as described in Equation (4). For example, the adaptive filter 448 may implement a FIR filter or an IIR filter as described above.

Figure 4C:
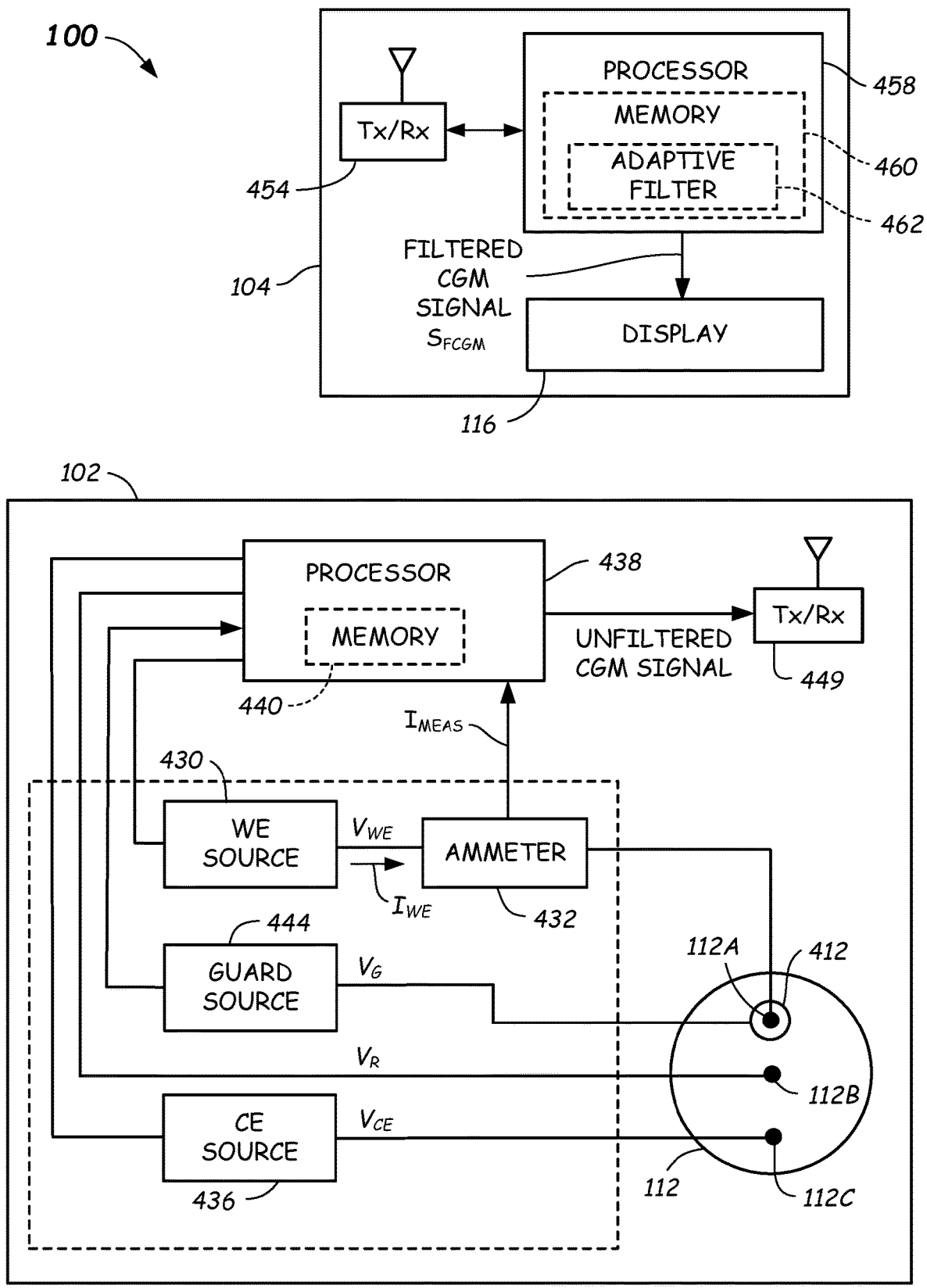
FIG. 4C is a schematic diagram showing another example of circuitry within a wearable device and an external device of a CGM system according to embodiments of the disclosure.

Reference is now made to FIG. 4C, which illustrates another embodiment of example circuitry in the CGM system 100 including the wearable device 102 and the external device 104. In the embodiment of FIG. 4C, the adaptive filtering is at least partially implemented in the external device 104 as described herein. In the embodiment of FIG. 4C, the external device 104 may include a transmitter/receiver 454, an external display 116, a processor 458, memory 460, and an adaptive filter 462 that may be stored in the memory 460 and implemented (e.g., executed) by the processor 458. In some embodiments, the transmitter/receiver 454 may receive an unfiltered CGM signal from the transmitter/receiver 449 located in the wearable device 102. In some embodiments, the transmitter/receiver 449 and the transmitter/receiver 454 may communicate wirelessly, such as by BLUETOOTH® or other suitable communication protocol. The transmitter/receiver 454 may also transmit instructions to the wearable device 102.

The adaptive filter 462 may be a digital filter wherein instructions for the adaptive filtering are stored in the memory 460 and executed by the processor 458 in the same or similar manner as described in connection with FIG. 4B. As described above, the adaptive filtering may be applied to the unfiltered CGM signal transmitted from the wearable device 102. In some embodiments, the external device 104 may receive the measured current signal $I_{MEAS}$ and the adaptive filter 462 may process the measured current signal $I_{MEAS}$ as described in connection with FIGS. 4A and 4B to generate a filtered CGM signal $S_{FCGM}$. For example, the adaptive filter 462 may generate a signal similar to $I_{FILT}$, which may be processed by the processor 458 to generate the filtered CGM signal $S_{FCGM}$. The filtered CGM signal $S_{FCGM}$ and/or other data calculated by the processor 458 may be output to the external display 116 and/or otherwise downloaded to another device (e.g., a computer).

Figure 5D:
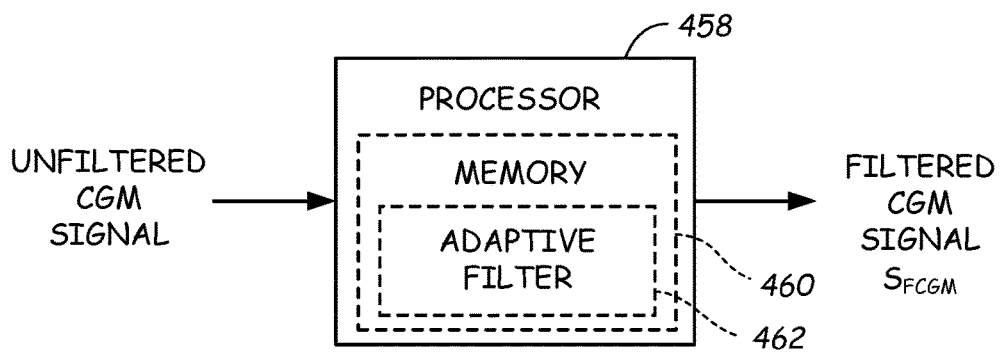
FIG. 5D is a block diagram showing an example of signal processing in an embodiment of a CGM system, wherein at least some of the adaptive filtering is performed in an external device according to embodiments of the disclosure.
Figure 5E:
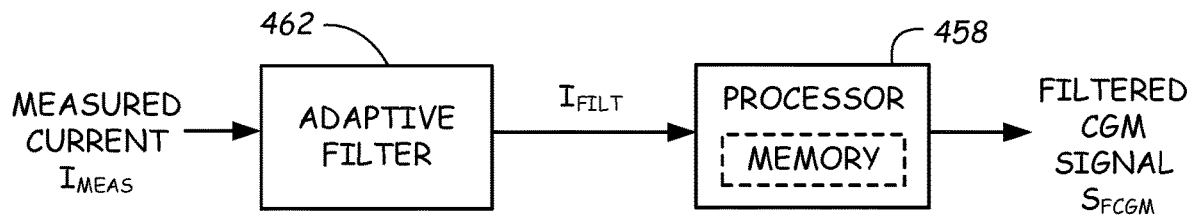
FIG. 5E is a block diagram showing another example of signal processing in an embodiment of a CGM system, wherein at least some of the adaptive filtering is performed in an external device according to embodiments of the disclosure.

Block diagrams of the adaptive filtering of the embodiment of FIG. 4C are shown in FIGS. 5D and 5E. As shown in FIG. 5D, the unfiltered CGM signal is received by the processor 458, which executes the adaptive filter 462 to generate the filtered CGM signal $S_{FCGM}$. The unfiltered CGM signal may be received from the wearable device 102. In FIG. 5E, the measured current signal $I_{MEAS}$ is received in the external device 104 and input to the adaptive filter 462. The adaptive filter 462 outputs the filtered measured current signal $I_{FILT}$, which is processed by the processor 458 to generate the filtered CGM signal $S_{FCGM}$.

In each of the embodiments, the optional local display 450 and/or the external display 116 may display graphs and/or numbers indicative of glucose concentrations. The information displayed may also include trends in glucose concentrations, such as downward and upward trends (e.g., displayed as an upward or downward arrow). Other information may also be displayed, such as units. Because the filtered CGM signal $S_{FCGM}$ has been filtered by the adaptive filtering, the graphs and/or other information displayed are more accurate than conventional information displayed for users. An example of the greater accuracy of information provided by the filtered CGM signals $S_{FCGM}$ is shown by the adaptively-filtered CGM signal 316 in FIG. 3B.

Examples of filtering and/or smoothing are described in the examples below. Reference is made to portions 314A and 314B of the unfiltered CGM signal 314 shown in FIG. 3B, which are in the thirteenth day of the CGM monitoring period and contain significant noise. For example, the portion 314A indicates that the user's glucose concentration is rising from about 120 mg/dl to about 180 mg/dl over a period of approximately five samples. The portion 314B indicates that the user's glucose concentration is falling from 180 mg/dl to about 115 mg/dl during the next four samples. The reference blood glucose concentrations 312 indicates that the user's glucose concentration is falling from about 155 mg/dl to about 140 mg/dl during the nine samples of the portion 314A and the portion 314B combined. If the user relies on the unfiltered CGM information in the portion 314A, the user will be informed that the glucose concentration is rising rapidly, when the glucose concentration is actually declining slightly. Should the user rely on the information in the portion 314B, the user can be informed that the glucose concentration is rapidly declining, when in reality the glucose concentration is slowly declining.

The filtered CGM signal 316 includes a portion 316A and a portion 316B that reflect glucose concentrations of the filtered CGM signal 316 during the same sampling times as the portion 314A and the portion 314B, respectively. As shown in FIG. 3B, the filtered CGM signal 316 rises from about 120 mg/dl to about 165 mg/dl during the portion 316A and falls from about 165 mg/dl to about 120 mg/dl during the portion 316B. The changes in glucose concentrations provided by the filtered CGM signal 316 are not as steep as those provided by the unfiltered CGM signal 314. Thus, information provided to the user may more accurately reflect the true glucose concentrations. For example, the rise in glucose concentration shown in the portion 316A and the subsequent fall in glucose concentration shown in the portion 316B are not as severe as those shown in the unfiltered CGM signal 314 and more closely follow the reference blood glucose concentrations 312. Thus, the use of adaptive filtering in a CGM system increases the reliability of data, including the CGM signal, generated by the CGM system.

Reference is made to Table 1 below, which summarizes results for various filtering options. MARD, as used in Table 1, is the mean absolute relative difference. A static filter includes a filter wherein the attenuation of the filter remains constant as a function of noise.

TABLE 1

Data Comparisons

| Parameter | No Filtering | Static Filtering | Adaptive Filtering |
|---|---|---|---|
| MARD 0-7 days | 13.75 | 13.89 | 13.98 |
| MARD 0-10 days | 13.73 | 13.90 | 14.00 |
| Smoothness 0-10 days | 0.154 | 0.118 | 0.111 |
| Smoothness 7-10 days | 0.194 | 0.143 | 0.124 |

For CGM glucose determinations, the MARD is described by Equation (6) as follows:

$$\text{MARD} = 100 * \Sigma [\text{Abs}([G_{CGM} - G_{REF}]/G_{REF})]/n) \quad \text{Equation (6)}$$

wherein $G_{CGM}$ is the CGM measured glucose concentration, $G_{REF}$ is a reference glucose concentration, measured by blood glucose measurement (BGM), for example, and n is the number of data points. The expression of MARD combines the mean and standard deviation of a sample population against the reference glucose values to produce a composite MARD value, where the smaller the MARD value, the better the accuracy. In some embodiments, a 10% MARD value may have an approximate accuracy of data within ±25%, or an approximate 25% accuracy. Conversely, a CGM system having an accuracy of ±10% would be projected to have a MARD value of 4%. As shown in Table 1, embodiments described herein using adaptive filtering are roughly comparable to MARD values of conventional filtering.

The smoothness may be calculated using different techniques. For example, smoothness may be calculated using the arithmetic average method. In other embodiments, smoothness may be calculated as the standard deviation of the glucose differences divided by the absolute value of the mean of the glucose differences. Other methods may be used to calculate the smoothness. As shown in Table 1, the signals having adaptive filtering applied thereto are smoother than conventional signals.

The CGM has been described as using devices that include biosensors located in interstitial fluid. Other CGM devices may be used. For example, optical sensors may also be used for continuous glucose or analyte monitoring. The optical device may employ fluorescence, absorbance, reflectance, and/or the like to measure glucose or other analytes. For example, an optical oxygen sensor relying on fluorescence or quenching of fluorescence may be employed to indirectly measure glucose by measuring the oxygen concentration in interstitial fluid, which has an inverse relationship to the glucose concentration.

Figure 8:
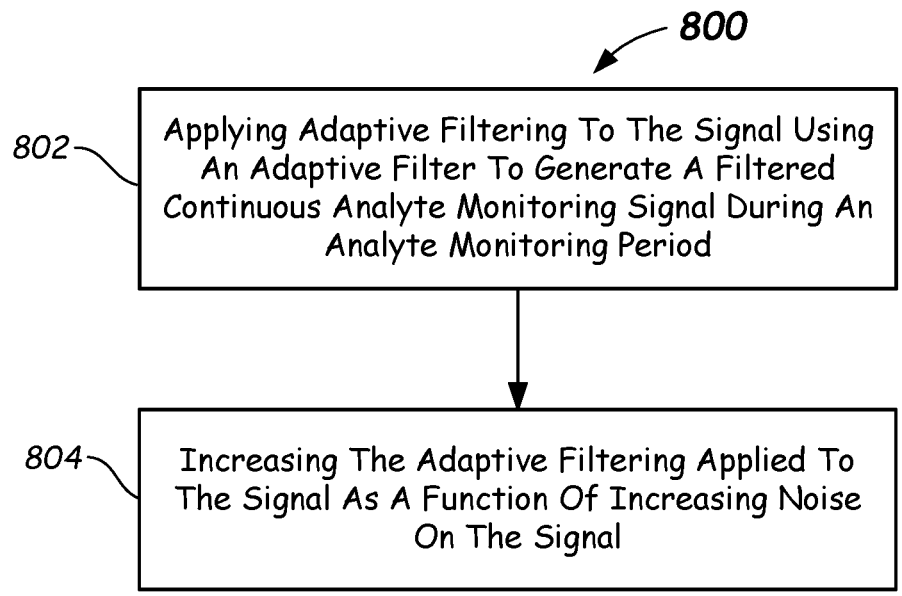
FIG. 8 illustrates a flowchart of a method of filtering a signal in a CAM system according to embodiments of the disclosure.

Reference is now made to FIG. 8, which illustrates a flowchart depicting a method 800 of filtering a signal in a continuous analyte monitoring system (e.g., CAM system 100). The method 800 includes, in 802, applying adaptive filtering to the signal using an adaptive filter (e.g., adaptive filter 448) to generate a filtered continuous analyte monitoring signal (e.g., signal $S_{FCGM}$) during an analyte monitoring period. The method also includes, in 804, increasing the adaptive filtering applied to the signal as a function of increasing noise on the signal.

Figure 9:
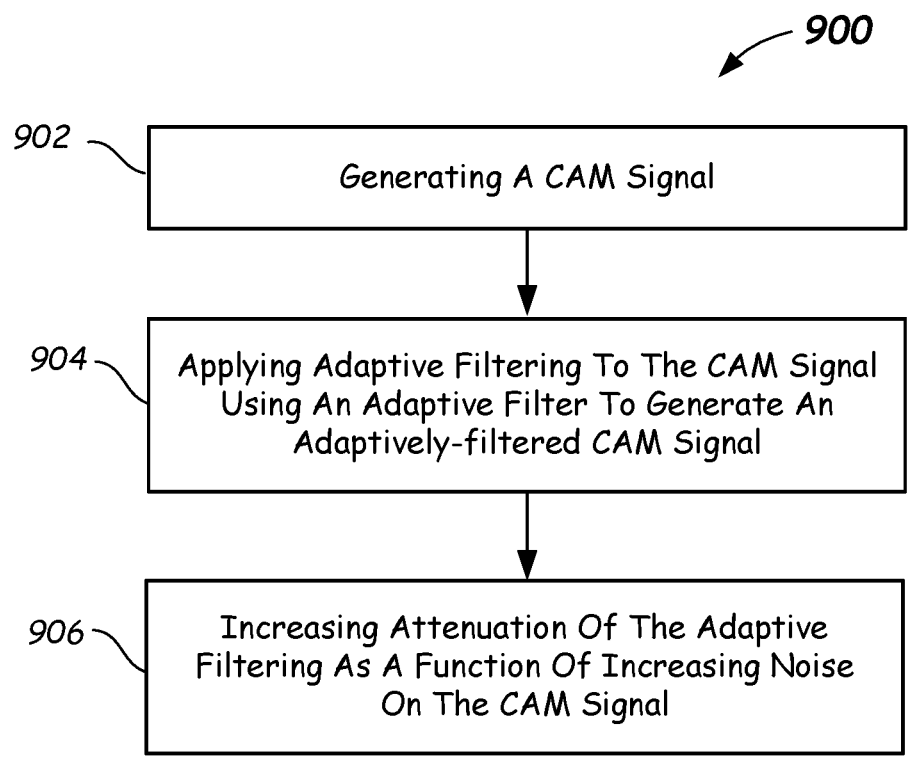
FIG. 9 illustrates a flowchart of a method of continuous analyte monitoring according to embodiments of the disclosure.

Reference is now made to FIG. 9, which illustrates a flowchart depicting a method 900 of continuous analyte monitoring (CAM). The method 900 includes, in 902, generating a CAM signal. The method 900 also includes, in 904, applying adaptive filtering to the CAM signal using an adaptive filter (e.g., adaptive filter 448) to generate an adaptively-filtered CAM signal (e.g., signal $S_{FCGM}$). The method 900 further includes, in 906, increasing attenuation of the adaptive filtering as a function of increasing noise on the CAM signal.

As discussed above, there are several adaptive filtering techniques, including: 1) where a signal within the CGM system 100, such as the measured current $I_{MEAS}$, is adaptively filtered and further processed to produce a filtered CGM signal $S_{FCGM}$, which may be transferred by the transmitter/receiver 449 to the external device 104, and 2) where $I_{MEAS}$ is processed to generate an unfiltered CGM signal, which is further processed to produce the filtered CGM signal $S_{FCGM}$.

The foregoing description discloses only example embodiments. Modifications of the above-disclosed apparatus and methods which fall within the scope of this disclosure will be readily apparent to those of ordinary skill in the art.

What is claimed is:

1. One or more non-transitory computer-readable media comprising computer-executable instructions that, when executed by at least one processor, perform a method of filtering a signal in a continuous analyte monitoring system, comprising:
   computing a noise level in an environment;
   providing one or more biosensors comprising a working electrode and a counter electrode;
   generating, using the one or more biosensors in the environment, the signal, wherein generating the signal comprises:
   applying a voltage across the working electrode and the counter electrode;
   measuring a current associated with the working electrode, wherein the current is proportional to an analyte concentration in the environment; and
   generating the signal using the current;
   applying adaptive filtering to the signal using an adaptive filter to generate a filtered continuous analyte monitoring signal during an analyte monitoring period, wherein applying the adaptive filtering to the signal comprises:
   switching one or more low-pass filters into a closed state, the one or more low-pass filters including one or more cut-off frequencies,
   wherein switching the one or more low-pass filters into the closed state is a function of the noise level such that all of the one or more low-pass filters are switched into the closed state when the noise level is zero;
   passing the signal through the one or more low-pass filters such that one or more frequencies of the signal are filtered out upon reaching the one or more cut-off frequencies; and
   changing the one or more cut-off frequencies as a function of the noise level; and
   increasing the adaptive filtering applied as a function of increasing the noise level to a following signal generated by the one or more biosensors.

2. The one or more non-transitory computer-readable media of claim 1, wherein applying the adaptive filtering comprises increasing attenuation of the adaptive filter as a function of increasing the noise level.

3. The one or more non-transitory computer-readable media of claim 1, wherein computing the noise level in the environment comprises:
   measuring a plurality of signal points in the environment; and
   computing a standard deviation based on the plurality of signal points.

4. The one or more non-transitory computer-readable media of claim 1, wherein the method further comprises:
   implanting the one or more biosensors at least partially in interstitial fluid; and
   generating a measured current signal from the one or more biosensors, wherein applying the adaptive filtering comprises applying the adaptive filtering to the measured current signal.

5. The one or more non-transitory computer-readable media of claim 1, wherein generating, using the one or more biosensors in the environment, the signal further comprises:
   applying additional adaptive filtering to the current.

6. The one or more non-transitory computer-readable media of claim 1, wherein the method further comprises calculating the analyte concentration from a continuous analyte monitoring signal that is indicative of the analyte concentration, wherein applying the adaptive filtering to the signal comprises applying the adaptive filtering to the continuous analyte monitoring signal to generate the filtered continuous analyte monitoring signal.

7. The one or more non-transitory computer-readable media of claim 6, wherein the method further comprises analyzing the filtered continuous analyte monitoring signal to generate a trend in analyte concentrations during the analyte monitoring period.

8. The one or more non-transitory computer-readable media of claim 1, wherein the method further comprises causing display of at least a portion of the filtered continuous analyte monitoring signal on a display.

9. The one or more non-transitory computer-readable media of claim 1, wherein the method further comprises causing display of a trend in analyte concentrations on a display.

10. The one or more non-transitory computer-readable media of claim 1, wherein increasing the adaptive filtering comprises increasing attenuation in a stop band of at least one low-pass filter of the one or more low-pass filters as a function of noise on the signal during the analyte monitoring period.

11. The one or more non-transitory computer-readable media of claim 1, wherein applying the adaptive filtering to the signal comprises applying infinite impulse response filtering to the signal.

12. The one or more non-transitory computer-readable media of claim 1, wherein applying the adaptive filtering to the signal comprises applying finite impulse response filtering to the signal.

13. The one or more non-transitory computer-readable media of claim 1, wherein applying the adaptive filtering to the signal comprises applying filtering in a form of: $S'(n) = \text{alpha}(R)*S(n) + (1-\text{alpha}(R))*S'(n-1)$, wherein the $S'(n)$ is the filtered continuous analyte monitoring signal, $S(n)$ is the signal, alpha(R) is a value less than or equal to 1.0, R is a noise estimate or measurement, and n is a sample number.

14. The one or more non-transitory computer-readable media of claim 13, wherein increasing the adaptive filtering applied to the signal as a function of a noise comprises decreasing the alpha(R) as a function of the noise.

15. The one or more non-transitory computer-readable media of claim 13, wherein the alpha(R) is calculated as baseAlpha−R*K, wherein the baseAlpha is a predetermined value and K is a constant that determines responsiveness of the alpha(R) to changes in noise.

16. The one or more non-transitory computer-readable media of claim 15, wherein the baseAlpha is in a range from 0.3 to 0.5.

17. The one or more non-transitory computer-readable media of claim 15, wherein the K is selected so that the alpha(R) is less than or equal to baseAlpha/2 when the R is at a maximum value.

18. The one or more non-transitory computer-readable media of claim 1, wherein applying the adaptive filtering to the signal comprises applying an exponential moving average to the signal.

19. The one or more non-transitory computer-readable media of claim 1, wherein an analyte in the continuous analyte monitoring system comprises glucose.

20. A method of continuous analyte monitoring (CAM), comprising:
   providing one or more biosensors comprising a working electrode and a counter electrode;
   generating in an environment, using the one or more biosensors, a CAM signal, wherein generating in the environment the CAM signal comprises:
    applying a voltage across the working electrode and the counter electrode;
    measuring a current associated with the working electrode, wherein the current is proportional to an analyte concentration in the environment; and
    generating the CAM signal using the current;
applying adaptive filtering to the CAM signal using an adaptive filter to generate an adaptively-filtered CAM signal, wherein applying the adaptive filtering comprises:
    computing a noise level in the environment;
    switching one or more low-pass filters into a closed state, the one or more low-pass filters including one or more cut-off frequencies,
    wherein switching the one or more low-pass filters into the closed state is a function of the noise level such that all of the one or more low-pass filters are switched into the closed state when the noise level is zero;
    passing the CAM signal through the one or more low-pass filters such that one or more frequencies of the CAM signal are filtered out upon reaching the one or more cut-off frequencies; and
    changing the one or more cut-off frequencies as a function of the noise level; and
increasing attenuation of the adaptive filtering as a function of increasing the noise level in the environment, wherein the adaptive filtering with increased attenuation is applied to a following CAM signal generated by the one or more biosensors.

21. The method of claim 20, wherein generating comprises calculating the CAM signal based on a signal generated by the one or more biosensors.

22. The method of claim 20, further comprising displaying at least a portion of the adaptively-filtered CAM signal on a display.

23. The method of claim 20, wherein applying the adaptive filtering to the CAM signal comprises applying infinite impulse response filtering to the CAM signal.

24. The method of claim 20 wherein applying the adaptive filtering to the CAM signal comprises applying filtering in a form of: S'(n)=alpha(R)*S(n)+(1−alpha(R))*S' (n−1), wherein S' (n) is the adaptively-filtered CAM signal, S(n) is the CAM signal, the alpha(R) is a value less than or equal to 1.0, R is a noise estimate or measurement, and n is a sample number.

25. The method of claim 24 wherein increasing the adaptive filtering applied to the CAM signal as a function of increasing the noise level in the environment comprises decreasing the alpha(R) as a function of the noise level.

26. The method of claim 20, wherein applying the adaptive filtering to the CAM signal comprises applying an exponential moving average to the CAM signal.

27. A continuous analyte monitoring system, comprising:
one or more biosensors comprising a working electrode and a counter electrode, wherein the one or more biosensors are configured to general a signal;
an adaptive filter configured to increase filtering of the signal as a function of increasing noise on the signal, comprising:
    one or more low-pass filters having one or more cut-off frequencies; and
    one or more filter switches electronically connected to the one or more low-pass filters, wherein the one or more filter switches are configured to toggle the one or more low-pass filters between a closed state and an open state; and
one or more non-transitory computer-readable media comprising computer-executable instructions that, when executed by at least one processor, perform a method of filtering the signal in the continuous analyte monitoring system, comprising:
computing a noise level in an environment;
generating, using the one or more biosensors in the environment, the signal, wherein generating the signal comprises:
    applying a voltage across the working electrode and the counter electrode;
    measuring a current associated with the working electrode, wherein the current is proportional to an analyte concentration in the environment; and
    generating the signal using the current;
applying adaptive filtering to the signal to generate a filtered continuous analyte monitoring signal during an analyte monitoring period, wherein applying the adaptive filtering to the signal comprises:
    switching the one or more low-pass filters into the closed state,
    wherein switching the one or more low-pass filters into the closed state is a function of the noise level such that all of the one or more low-pass filters are switched into the closed state when the noise level is zero;
    passing the signal through the one or more low-pass filters such that one or more frequencies of the signal are filtered out upon reaching the one or more cut-off frequencies; and
    changing the one or more cut-off frequencies as a function of the noise level; and
increasing the adaptive filtering applied to the signal as a function of the noise level increasing to a following signal generated by the one or more biosensors.

* * * * *